United States Patent [19]

Cort

[11] 4,181,255
[45] Jan. 1, 1980

[54] ODOR FILTERING DEVICE

[75] Inventor: J. George Cort, Port Washington, N.Y.

[73] Assignee: CDC Chemical Corporation, New York, N.Y.

[21] Appl. No.: 801,983

[22] Filed: May 31, 1977

[51] Int. Cl.² .............................................. A61L 9/04
[52] U.S. Cl. ..................................................... 239/54
[58] Field of Search ......................... 239/6, 34, 53–56

[56] References Cited

U.S. PATENT DOCUMENTS

| | | | |
|---|---|---|---|
| 1,536,741 | 5/1925 | Alden | 239/54 |
| 2,596,659 | 5/1952 | D'Eustachio | 181/33 GA |
| 3,567,119 | 3/1971 | Wilbert et al. | 239/34 |
| 3,753,500 | 8/1973 | Voegeli | 210/446 |
| 3,945,950 | 3/1976 | Vosganiantz | 239/53 |
| 4,009,253 | 2/1977 | Schleppnik | 424/45 |
| 4,051,159 | 9/1977 | Tsoucalas et al. | 239/34 |

FOREIGN PATENT DOCUMENTS 2341938  8/1973  Fed. Rep. of Germany ............ 239/54

*Primary Examiner*—Robert W. Saifer
*Attorney, Agent, or Firm*—Blum, Kaplan, Friedman, Silberman & Beran

[57] ABSTRACT

An odor filtering device for space dispensing a volatile oil by soaking a porous substrate with a malodor counteractant composition. The exposed surface of the substrate permits evaporation of malodor counteractant creating an internal vapor pressure differential which drives the counteractant from the interior of the substrate to the surface to replace the surface loss. Particular devices are formed and arranged to permit controlled release of the malodor counteractant over an extended period of time.

18 Claims, 7 Drawing Figures

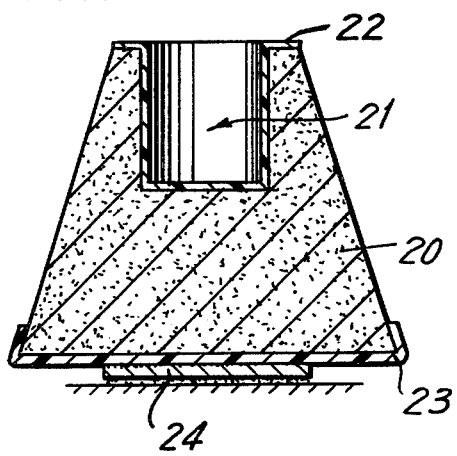
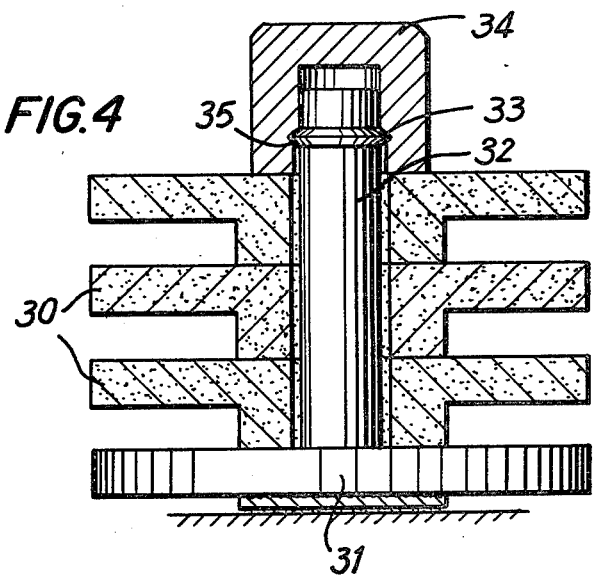
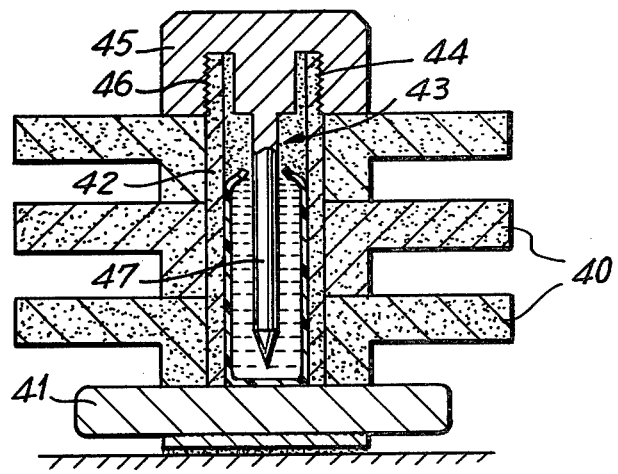
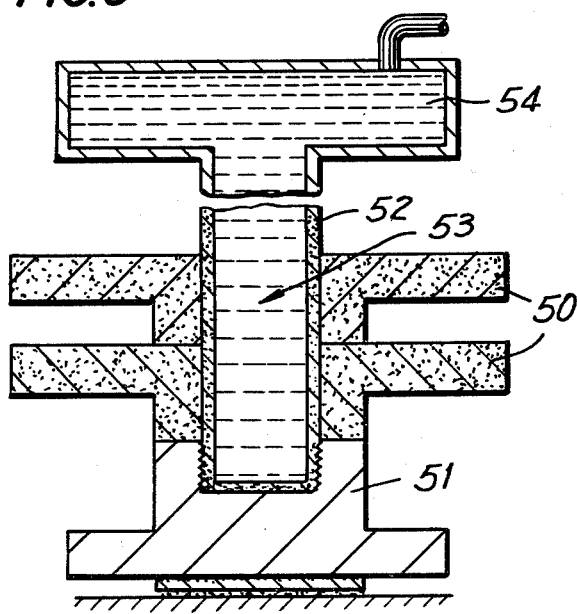
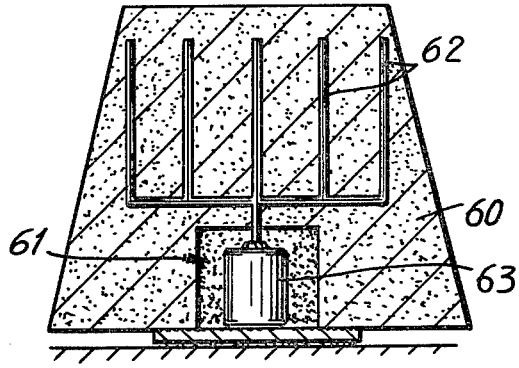

ODOR FILTERING DEVICE

BACKGROUND OF THE INVENTION

This invention relates generally to an odor control device and particularly to an odor filtering device comprising a substrate soaked with an essential oil malodor counteractant composition.

Methods and devices for odor control, such as, deodorizing and masking, are well known in the art. These methods and devices operate by masking or overpowering an unpleasant odor with other odors forming a different bouquet, or introduce a powerful pleasant smell which causes the malodor to be less noticeable. Other known devices contain surface active agents, such as quaternary ammonium salts or biphenyls. The biphenyls anesthetize nerve endings in the olfactory gland and may be toxic. Other methods involve molecular change such as utilizing ozone which tends to increase an individuals' rate of metabolism. Thus, it is apparent that these prior devices and methods are not completely satisfactory in overcoming the effects of unpleasant odors.

SUMMARY OF THE INVENTION

Generally speaking, in accordance with the invention, an odor filtering device for space dispensing a volatile oil comprising a substrate soaked with an essential oil for controlled release of a malodor counteractant is provided. The substrate is a substantially rigid material formed with microscopic voids therein. The substrate is soaked with an essential oil composition. The essential oil composition at the exposed surfaces of the substrate evaporates, thereby creating an internal pressure differential so that the composition entrained in the interior of the substrate diffuses to the surface to replace the evaporated composition. By regulating the void size and the size and shape of the substrate, a controlled rate of release and air composition of malodor counteractant may be obtained.

Accordingly, it is an object of this invention to provide an improved odor control device.

Another object of the invention is to provide an odor filtering device which permits a controlled rate of release of a malodor counteractant.

A further object of the invention is to provide an odor control device including a malodor counteractant which is neither an irritant nor toxic.

Still another object of the invention is to provide an odor control device which is compact.

Another object of the invention is to provide an odor control device which is effective for an extended period of time.

Still other objects and advantages of the invention will in part be obvious and will in part be apparent from the specification.

The invention accordingly comprises the product possessing the features, properties and relation of components which will be exemplified in the product hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 through FIG. 7 are cross-sectional views of further embodiments of the invention.

DESCRIPTION OF THE PREFERRED EMBODIMENTS

Figure 1:
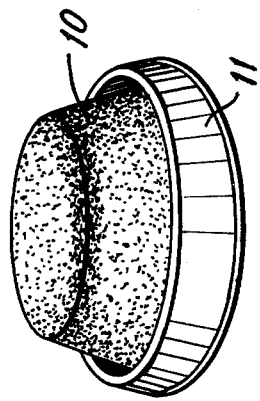
FIG. 1 is a perspective view of an odor filtering device constructed in accordance with the invention.

The odor filtering device of the present invention for space dispensing a volatile oil comprises a substrate containing therein a malodor counteractant composition. The malodor counteractant composition is a mixture of an essential oil which produces a reversible anosmia for malodors and an accelerator for controlling rate of release. The substrate may be any substantially rigid material containing voids formed therein.

A malodor counteractant which produces the desired reversible selective anosmia for malodors is available from Monsanto Chemical Company under the trademark Veilex. The Veilex malodor counteractant reversibly prevents acceptance of malodors at protein receptor sites, so that the olfactory system does not transmit and the odor is not perceived. The counteractant is effective and odor filtering activity lasts as long as an air level of 1 part per million or more is maintained. When exposure to the malodor counteractant is ended, a person's selective anosmia stops after a few seconds and full sensitivity to the malodor is restored. See for example, U.S. Pat. No. 4,009,253 issued on Feb. 22, 1977 which describes a 4-cyclohexyl-4-methyl-2-pentanone malodor counteractant.

It is recognized that all odors, both fragrant and malodor, are made up of some combination of seven primary odors. The following Table identifies the primary odors and their familiar comparable odor.

| PRIMARY ODOR | FAMILIAR COMPARABLE ODOR |
| --- | --- |
| Musk | Moth repellent |
| Camphoraceous | Angelica root oil |
| Flora | Roses |
| Peppermint | Mint, as in candy mints |
| Etheral | Dry cleaning fluid |
| Pungent | Vinegar |
| Putrid | Rotten egg |

Each primary odor has a different geometrical molecular shape and the sense of smell is based upon the physical fit between this molecular shape and a specific olfactory receptor. These receptors are located in the nose ridge. When a receptor and odor molecule fit an electrical impulse is discharged to the brain causing the sensation of a specific smell. The odor counteractant molecules duplicate the structure of putrid molecules blocking the true putrid molecule from causing malodor perception. Therefore, there is no malodor awareness for such odors as perspiration, fish, tobacco, smoke, rotten egg, urine, feces and combinations of these.

The Veilex malodor counteractant produces the desired anosmia without anesthetizing or desensitizing nerve endings in the olfactory glands. The composition utilized in the invention is not categorized as an irritant, nor is it a toxic material. In addition to blocking out malodors, the odor counteractant has no effect on fragrant odors. Thus, the desired filtering technique of the odor filtering device is obtained in a safe and effective manner.

As noted above, the Veilex malodor counteractant is effective when present in air at about 1 part per million and above. The Veilex malodor counteractant is modified for use in the invention by mixing with a perfume accelerator in order to obtain proper air compositions. Effective perfume accelerators for the Veilex malodor counteractant are, for example, highly refined and deodorized kerosene, propylene glycol, ethylene glycol and comparable low molecular weight dibasic and polyhydric alcohols, which are more volatile than the malodor counteractant. The preferred accelerators include the kerosene and propylene glycol.

When preparing the malodor counteractant composition for use in the invention, accelerator in amounts ranging up to about 75 weight percent of the malodor counteractant composition are mixed. Preferably, accelerator is used in amounts from about 75 to 125 percent of the weight of the malodor counteractant essential oil. In an exemplary embodiment, about equal amounts by weight of malodor counteractant and accelerator are mixed. The malodor counteractant composition is added to the substrate by soaking the substrate in a counteractant bath until saturated. In addition, an effective amount of a fragrance or perfume may be added to the malodor counteractant composition. As the malodor counteractant essential oil is odorless, the added fragrance acts as an indicator that the malodor counteract is present.

The preferred substrate utilized in the invention is formed from a polyethylene material that has undergone a series of curing processes resulting in microscopic voids being formed therein. The polyethylene material is marketed under the trademark Interflow by Chromex Chemical Company of Brooklyn, N.Y. The voids are substantially uniform in size and may range from 10 to 150 microns in cross-section. Preferably, the voids are from about 30 to 90 microns. In an exemplary embodiment the voids are from 50 to 70 microns in cross-section. When using a substrate having voids of this latter size, it has been found that the substrate will absorb from about 75 to 125 percent of its weight of malodor counteractant composition and provide the desired air concentrations for about 25 to 40 days under normal conditions. Thus, by regulating void size within the substrate and amount of accelerator, together with the shape and surface area of the substrate, an odor filtering device capable of controlled release of the malodor counteractant for a predetermined period of time may be obtained.

The substrate utilized in the invention may be formed into any convenient shape. However, it has been found that a desirable rate of release of malodor counteractant may be obtained from a substantially cylindrical or frusto-conical shape. These shapes also may be conveniently inserted into a holder for securing the device out of view. For example, FIG. 1 shows an odor control device constructed and arranged in accordance with the invention with substrate 10 formed as a frustum. Holder 11 is formed as a flat disc with an upward projecting lip for securing substrate 10 therein. A pressure sensitive adhesive tab (not shown) may be attached to the base of holder 11 for securing the device to any convenient location.

Figure 2:
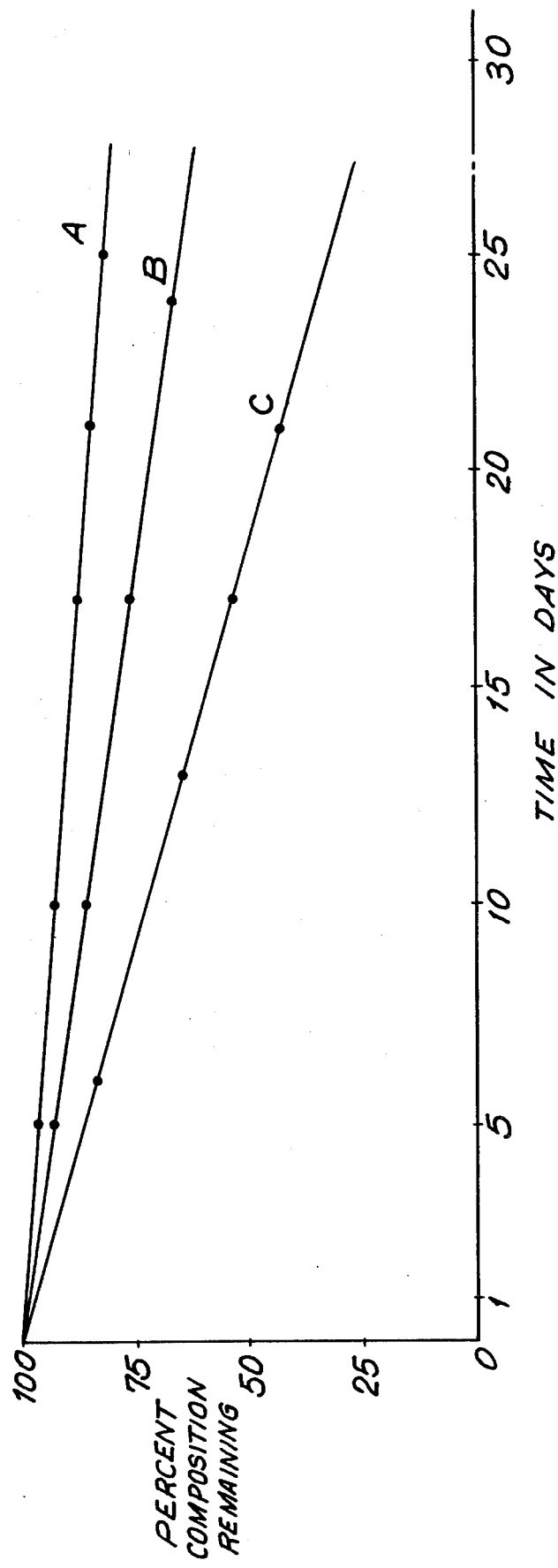
FIG. 2 is a graphic illustration showing remaining odor counteractant in the device of FIG. 1 over an extended period of time.

FIG. 2 graphically illustrates the rate of release of malodor counteractant in representative devices constructed in accordance with the embodiment shown in FIG. 1. In each case, the substrate is a frustam formed from Interflow polyethylene material with voids of about 60 microns in cross-section. The substrate is about three-fourths of an inch in height and one and three-quarters inches at its base and weighs about 10 grams before saturation with malodor counteractant. The malodor counteractant is entrained in the substrate by soaking the substrate in the malodor counteractant composition shown in the following Table.

| Example | Composition (weight percent) | Starting Weight (grams) |
|---|---|---|
| A | 100% Veilex | 20.6 |
| B | 50% Veilex | |
| | 50% propylene glycol | 21.4 |
| C | 50% Veilex | 18.24 |
| | 50% kerosene | |

In each case, the device was tested in still air at an average room temperature of 70° F. The kerosene used in Example C is a highly purified and deodorized kerosene. The data points shown in FIG. 2 are actual experimental results from these examples.

It can be seen from the results in FIG. 2 that the devices containing an accelerator (Examples B and C) release the malodor counteractant composition at a faster rate than a device containing no accelerator (Example A). After 20 days of testing, Example C released about 55 weight percent of the entrained malodor counteractant, while in Example A only about 17.5 weight percent was released. This three-fold increase in release of composition represents a two-fold increase in release of the essential oil and odor filtering capability. Thus, it is apparent that a wide range of rates of release can be obtained within the scope of the invention.

FIG. 3 shows an embodiment of the invention wherein the effective substrate surface area of an odor filtering device may be varied by a user. Substrate 20 is a frustum with a substantially cylindrical cavity 21 in its top surface. A cap 22 formed in a cylindrical shape to mate with cavity 21 and having an outwardly projecting peripheral flange is shown releasably positioned in cavity 21 covering the cavity walls and top surface of substrate 20. When a user desires increased odor filtration, cap 22 is removed exposing additional substrate surface area resulting in increased volatilization of odor counteractant. Substrate 20 is shown secured in holder 23. Adhesive disc 24 which has adhesive on both surfaces is mounted on the bottom surface of holder 23 for securing the device to a desired location.

Referring now to FIG. 4, substrates 30 are formed as substantially cylindrical discs, each having a hollow center and an integral boss to separate one disc from another for increased exposed substrate area between discs. Base 31 is formed with stem 32 attached at its center. The top portion of stem 32 is provided with securing means, such as, projection 33. Substrate discs 30 are mounted successively on base 31 about stem 32 and securing cap 34 formed with matching depression 35 is positioned on stem 32 to lock substrates 30 in position. This embodiment allows a user to replace a desired number of exhausted discs depending on malodor intensity or room size.

In FIG. 5, each substrate disc 40 is formed similarly with a hollow center and in integral boss. Base 41 is formed with porous stem 42 defining a substantially cylindrical chamber 43 perpendicular to base 41. The upper portion of stem 42 is formed with securing means, such as, threads 44. Securing cap 45 is formed with matching threads 46 and a piercing shaft 47 for projecting into chamber 40. Substrate discs 40 are stacked in position on stem 42 and secured by securing cap 45. When the device needs to be refilled with malodor counteractant, a capsule containing malodor counteractant is placed in cavity 43. Upon replacement of cap 45, the capsule is pierced by piercing shaft 47 allowing substrate discs 40 to absorb the malodor counteractant. An advantage of this embodiment is that a user may regenerate the device of a new capsule of malodor counteractant in chamber 43.

Referring now to FIG. 6, an odor filtering device which may be used in large installations and air conditioning systems employing a duct distribution system is shown. Substrate discs 50 are formed with integral bosses and hollow centers. Base 51 is formed with a hollow porous stem 52 perpendicular thereto. Stem 52 defines cavity 53 which is integrally connected to reservoir 54 containing malodor counteractant composition to allow for continuous or selective saturation of substrate discs 50.

Referring now to FIG. 7, substrate 60 formed in the shape of a frustum includes cavity 61 in the bottom and internal electrodes 62. Cavity 61 contains battery 63 for providing electric current to electrodes 62 for increasing substrate temperature. This embodiment allows increased volatility rate of malodor counteractant due to increased internal substrate temperature, and is useful in areas of high malodor concentration.

It will thus be seen that the objects set forth above, among those made apparent from the preceding description, are efficiently attained and, since certain changes may be made in the above product without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An odor filtering device for space dispensing a volatile oil comprising a substantially rigid substrate means having voids of substantially uniform size throughout for entraining an essential oil therein, the size of the voids between about 10 and 150 microns in cross-section and a volatile essential oil entrained in the substrate, the oil comprising a mixture of a malodor counteractant capable of producing reversible selective anosmia and a perfume accelerator, whereby said essential oil is volatilized to the space at a predetermined rate.

2. The device of claim 1, wherein said mixture includes at least about 25 weight percent malodor counteractant.

3. The device of claim 1, wherein said accelerator is a low molecular weight dibasic alcohol.

4. The device of claim 1, wherein said accelerator is propylene glycol.

5. The device of claim 1, wherein said accelerator is kerosene.

6. The device of claim 1, wherein said mixture is entrained in an amount from about one-half to one and one-half times the weight of said substrate.

7. The device of claim 6, wherein said substrate means is frusto-conical in shape.

8. The device of claim 7, wherein said device includes a holder formed in the shape of a disc with an upward projecting peripheral lip for securing said substrate therein and a securing means for attaching to the bottom of said holder for securing said device to a desired location.

9. The device of claim 7, wherein said frusto-conical substrate is formed with a cavity in its top surface for increasing surface area, and including a cap means formed to register with said cavity and for covering said cavity surface area.

10. The device of claim 7, including at least one electrode means in said substrate for receiving an electric current to increase the temperature of said substrate.

11. The device of claim 1, wherein said substrate is formed from a polyethylene material.

12. The device of claim 11, wherein said mixture comprises about 50 weight percent malodor counteractant and about 50 weight percent refined and deodorized kerosene.

13. The device of claim 12, wherein said mixture includes an effective amount of a fragrance.

14. The device of claim 12, including a malodor counteractant reservoir, wherein said stem means is porous and formed to define an internal chamber, and said internal chamber is integrally connected with said reservoir for receiving malodor counteractant.

15. The device of claim 1, wherein said substrate means is formed from at least two substantially cylindrical discs each having an integral boss and a hollow center and a cylindrical base with a projecting stem means perpendicular to said base and a securing cap means, said stem means having a securing portion at the upper end thereof, wherein said substrate discs are mounted successively on said stem for securing by said securing cap means.

16. The device of claim 15, wherein said stem means is porous and formed to define an internal cylindrical chamber and said securing cap means includes a projecting piercing means for piercing a soft capsule of malodor counteractant positionable in said chamber.

17. An odor filtering device for space suspensing a volatile oil comprising a substantial rigid substrate formed from a polyethylene material with voids of substantially uniform microscopic size throughout, the size of said voids therein of from about 30 to 90 microns in cross-section and an essential oil comprising a malodor counteractant capable of producing reversible selective anosmia admixed with between about 25 and 75 weight percent of a perfume accelerator based on the weight of said mixture entrained in said voids, whereby said essential oil is volatilized to the space at a predetermined rate.

18. The device of claim 17, wherein said voids are from about 50 to 70 microns in cross-section.

* * * * *